United States Patent
Zubeldia et al.

(10) Patent No.: US 6,397,224 B1
(45) Date of Patent: May 28, 2002

(54) ANONYMOUSLY LINKING A PLURALITY OF DATA RECORDS

(75) Inventors: Kepa Zubeldia, Kaysville, UT (US); Gordon W. Romney, 3740 Lois La., Salt Lake City, UT (US) 84124

(73) Assignee: Gordon W. Romney, Midway, UT (US)

( * ) Notice: Subject to any disclaimer, the term of this patent is extended or adjusted under 35 U.S.C. 154(b) by 0 days.

(21) Appl. No.: 09/459,161

(22) Filed: Dec. 10, 1999

(51) Int. Cl.$^7$ .............................................. G06F 17/00
(52) U.S. Cl. ...................................... 707/102; 707/101
(58) Field of Search .......................... 707/1; 709/229; 705/2, 3, 10, 50

(56) References Cited

U.S. PATENT DOCUMENTS

| | | | |
|---|---|---|---|
| 5,581,749 A | 12/1996 | Hossain et al. | 395/600 |
| 5,802,199 A | 9/1998 | Pare, Jr. et al. | 382/115 |
| 5,809,494 A * | 9/1998 | Nguyen | 707/1 |
| 5,832,494 A | 11/1998 | Egger et al. | 707/102 |
| 5,907,677 A | 5/1999 | Glenn et al. | 395/200.36 |
| 6,195,661 B1 | 2/2001 | Filepp et al. | 707/102 |

* cited by examiner

*Primary Examiner*—Safet Metjahic
*Assistant Examiner*—Apu M Mofiz
(74) *Attorney, Agent, or Firm*—Kory D. Christensen; Madson & Metcalf

(57) ABSTRACT

A system for anonymously linking a plurality of data records, each data record comprising a plurality of elements for identifying an associated individual, includes a first identity reference encoding module configured to encode a first encoded identity reference from a first subset of the identifying elements of a data record; a second identity reference encoding module configured to encode a second encoded identity reference from a second subset of the identifying elements of the data record; and an anonymization code assignment module configured to assign to each of the first and second encoded identity references an identical anonymization code for anonymously representing the individual associated with the data record.

42 Claims, 3 Drawing Sheets

ANONYMOUSLY LINKING A PLURALITY OF DATA RECORDS

BACKGROUND OF THE INVENTION

1. Field of the Invention

The present invention relates generally to data management, and more particularly, to a system and method for anonymously linking a plurality of data records.

2. Relevant Technology

Recent years have seen an increased expectation of confidentiality in personally identifiable information stored in computer databases. For example, the Health Insurance Portability and Accountability Act of 1996 (HIPAA) requires the maintenance of appropriate security measures to preserve the confidentiality of health information. In particular, the HIPAA establishes severe penalties for "wrongful disclosure" of health information that is individually identifiable.

However, for legitimate purposes, it is important to be able to associate multiple records (from one or more data sources) related to a single individual. For example, the linking of related data records is crucial in performing certain research studies, such as horizontal and longitudinal studies. A horizontal study is conducted at one point in time, across multiple lines of service, such as services provided by physicians, pharmacists, hospitals, laboratories, and the like. A longitudinal study, on the other hand, is conducted on services provided over time to the same patient or population.

Consequently, the removal of personally identifying information from data records (hereinafter referred to as "de-identification" or "anonymization") to comply with privacy regulations, without degrading the ability to conduct both horizontal and longitudinal studies, is of critical importance to researchers.

However, the linking of anonymized data records presents at least two problems not fully solved by conventional approaches. First, all of the records pertaining to a single individual need to be identified. As explained below, this can be difficult because records from different data sources may use different types of personal identifiers, many of which may not uniquely identify an individual, or may even change over time for the same individual.

Second, the records of an individual should be anonymously linked in such a way that it would be difficult or impossible to discover the identity of the individual to whom the records pertain. As explained hereafter, conventional approaches, such as a Master Patient Index (MPI), do not protect an individual's privacy, since they may be used to recover personally identifying information from an assigned identification code.

Unfortunately, the lack of a single, universal identifier in the United States complicates the problem of identifying all of the records of a single individual. For example, the U.S. healthcare system does not have a unique identifier for each patient. As such, a multitude of different identification schemes have developed.

For instance, a person is typically issued one healthcare identifier by a medical plan, another by a dental plan, and yet another from a pharmacy benefits manager, and possibly several more from secondary coverage sources. Some identifiers may be based on a Social Security Number (SSN) with the optional addition of a "person code." However, in many cases, the healthcare identifiers are independently created, alphanumeric codes of between 5 and 18 digits.

The identification problem is further complicated by the volatility of personal identifiers. For example, people may change their names, either through marriage, divorce, adoption, or the like. Other personal identifiers, such as an individual's address, city, and ZIP code are even more volatile than the individual's name. Even the once stable characteristic of gender is now subject to change. The date of birth is frequently the only stable characteristic, although it is not useful, alone, in uniquely identifying an individual.

As noted above, the associated problem of anonymously linking a plurality of related records lies in the fact that conventional approaches typically do not prevent identification of the individual to whom the records pertain. For example, hospitals often assign a unique number or code to each patient for purposes of linking patient transaction records from different sources, e.g., radiological reports, pathology reports, physician's notes, and the like.

Although the records may include a variety of personal identifiers, such as a name and date of birth, the patient code is generally the only identifier used within the hospital to correlate the patient's records. One purpose of exclusively relying on the patient code is to prevent confusion between two or more patients sharing the same name or other personal identifiers.

Typically, the hospital maintains a Master Patient Index (MPI), which associates the patient's personal identifiers with the assigned patient code. By providing one or more personal identifiers, doctors or hospital staff may obtain from the MPI the patient's assigned code.

Unfortunately, the MPI may also be used to reverse the process and obtain the patient's personal information from the patient code. As such, the MPI is not well suited for anonymously linking the patient's records.

Industries other than healthcare would similarly benefit from a system for anonymously linking data records. For example, consumer studies could be conducted using large clearinghouses of consumer data without jeopardizing the privacy of consumers by the misuse of such data. Moreover, even where anonymization of the data records is not required, a system for identifying records related to the same individual would be highly desirable.

Accordingly, what is needed is a system and method identifying a plurality of data records related to the same individual. Moreover, what is needed is a system and method for anonymously linking the plurality of related data records, such that the records may be de-identified and used in research studies and the like.

SUMMARY OF THE INVENTION

The present invention solves many or all of the foregoing problems by providing an anonymized linking system and method. In one aspect of the invention, a first identity reference encoding module encodes a first encoded identity reference from a first subset of the identifying elements of a data record. The first encoded identity reference may comprise, for example, a one-way hash of the first subset of identifying elements.

In another aspect, a second identity reference encoding module encodes a second encoded identity reference from a second subset of the identifying elements of the data record. The first and second subsets may be disjoint, or may include one or more identifying elements in common.

In yet another aspect, an anonymization code assignment module assigns to each of the first and second encoded identity references an identical anonymization code for anonymously representing the individual associated with the data record. In one embodiment, the anonymization code may include a unique serial number.

In still another aspect, an anonymization code lookup module determines whether each of the first and second encoded identity references has an assigned anonymization code stored within an anonymization code database. In one embodiment, the anonymization code database comprises an "anonymous index" for linking at least one encoded identity reference to an assigned anonymization code.

If neither the first nor second encoded identity references are found to have an assigned anonymization code, the anonymization code assignment module may provide a new anonymization code and assign the new anonymization code to both the first and second encoded identity references. If, however, one encoded identity reference is found to have an assigned anonymization code while the other encoded identity reference does not, the anonymization code assignment module may assign the same anonymization code found to be associated with the one encoded identity references to the other encoded identity reference.

In another aspect, an anonymization code insertion module may insert the assigned anonymization code into the data record, while an identifying element removal module optionally removes the plurality of identifying elements from the data record, thus anonymizing or de-identifying the data record.

These and other objects, features, and advantages of the present invention will become more fully apparent from the following description and appended claims, or may be learned by the practice of the invention as set forth hereinafter.

BRIEF DESCRIPTION OF THE DRAWINGS

These and other more detailed and specific objects and features of the present invention are more fully disclosed in the following specification, with reference to the accompanying drawings, in which.

DETAILED DESCRIPTION OF THE PREFERRED EMBODIMENTS

Certain preferred embodiments of the invention are now described with reference to the Figures, where like reference numbers indicate identical or functionally similar elements. The components of the present invention, as generally described and illustrated in the Figures, may be implemented in a wide variety of configurations. Thus, the following more detailed description of the embodiments of the system and method of the present invention, as represented in the Figures, is not intended to limit the scope of the invention, as claimed, but is merely representative of presently preferred embodiments of the invention.

Throughout the following description, various components of a system in accordance with the present invention are described as "modules." In one embodiment, the modules may be implemented as software, hardware, firmware, or any combination thereof.

For example, as used herein, a module may include any type of computer instruction or computer executable code located within a memory device and/or transmitted as electronic signals over a system bus or network. An identified module may include, for instance, one or more physical or logical blocks of computer instructions, which may be organized as an object, a procedure, a function, a remote procedure call, or the like.

The identified modules need not be located together, but may include disparate instructions stored in different locations, which together implement the described functionality of the module. Indeed, a module may include a single instruction, or many instructions, and may even be distributed among several discrete code segments, within different programs, and across several memory devices.

Figure 1:
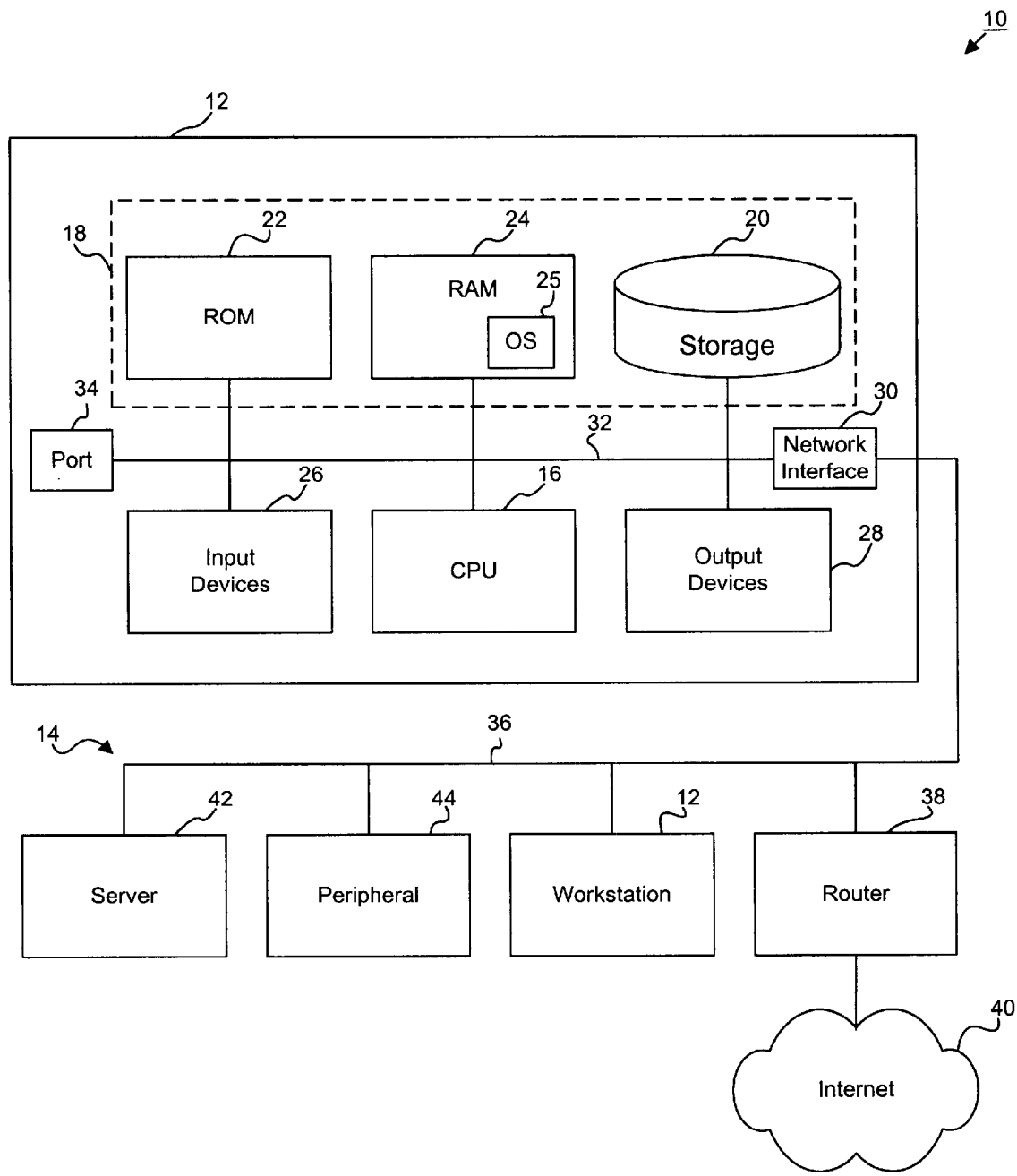
FIG. 1 is a schematic block diagram of a computer system suitable for implementing one embodiment of the invention.

FIG. 1 is a schematic block diagram illustrating a computer system 10 in which a plurality of modules may be hosted on one or more computer workstations 12 connected via a network 14. The network 14 may comprise a wide area network (WAN) or local area network (LAN) and may also comprise an interconnected system of networks, one particular example of which is the Internet.

A typical computer workstation 12 may include a central processing unit (CPU) 16. The CPU 16 may be operably connected to one or more memory devices 18. The memory devices 18 are depicted as including a non-volatile storage device 20, such as a hard disk drive or CD-ROM drive, a read-only memory (ROM) 22, and a random access memory (RAM) 24.

Preferably, the computer workstation 12 operates under the control of an operating system (OS) 25, such as OS/2®, WINDOWS NT®, WINDOWS®, UNIX®, and the like. In one embodiment, the OS 25 provides a graphical user interface (GUI) to enable the user to visually interact with the modules of the present invention. In one embodiment, the OS 25 may be loaded from the non-volatile storage device 20 into the RAM 24 at the time the computer workstation 12 is booted.

The computer workstation 12 may also include one or more input devices 26, such as a mouse and/or a keyboard, for receiving inputs from a user. Similarly, one or more output devices 28, such as a monitor and/ or a printer, may be provided within, or be accessible from, the computer workstation 12.

A network interface 30, such as an Ethernet adapter, may be provided for coupling the computer workstation 12 to the network 14. Where the network 14 is remote from the computer workstation 12, the network interface 30 may comprise a modem, and may connect to the network 14 through a local access line, such as a telephone line.

Within any given computer workstation 12, a system bus 32 may operably interconnect the CPU 16, the memory devices 18, the input devices 26, the output devices 28, the network interface 30, and one or more additional ports 34, such as parallel ports and/or RS-232 serial ports.

The system bus 32 and a network backbone 36 may be regarded as data carriers. Accordingly, the system bus 32 and the network backbone 36 may be embodied in numerous configurations, such as wire and/ or fiber optic lines, as well as "wireless" electromagnetic links using visible light, infrared, and radio frequencies.

In general, the network 14 may comprise a single local area network (LAN), a wide area network (WAN), several adjoining networks, an intranet, an extranet, or as in the manner depicted, a system of interconnected networks such as the Internet 40. The individual computer workstations 12 may communicate with each other over the backbone 36 and/or over the Internet 40 using various communication techniques.

For instance, different communication protocols, e.g., ISO/OSI, IPX, TCP/IP, may be used within the network 14. In the case of the Internet 40, however, a layered communications protocol (i.e. TCP/IP) generally best enables communications between the differing networks 14 and computer workstations 12.

The computer workstations 12 may be coupled via the network 14 to application servers 42, and/or other resources or peripherals 44, such as scanners, digital cameras, fax machines, and the like. External networks, such as the Internet 40, may be coupled to the network 14 through a router 38 or firewall.

Figure 2:
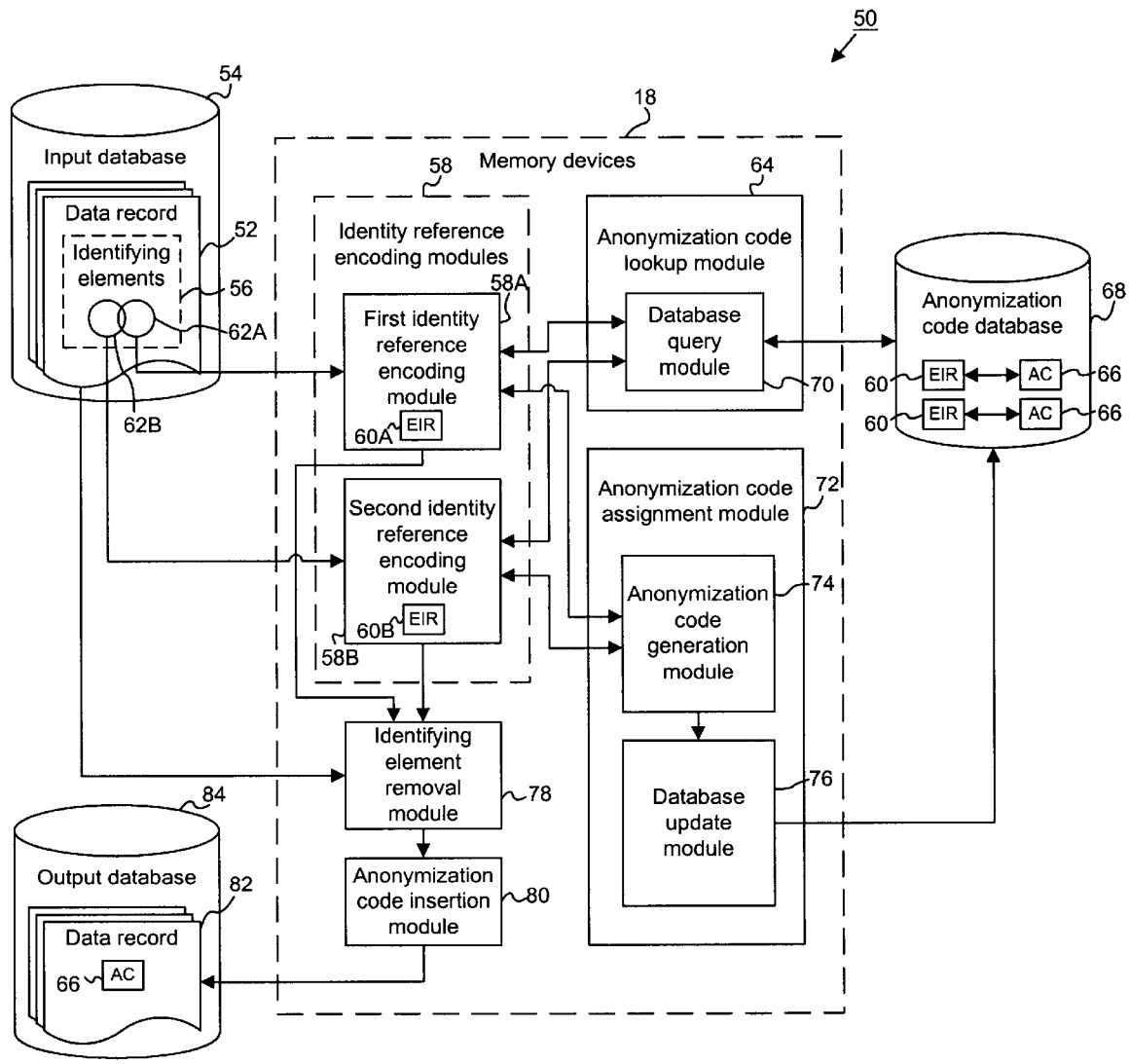
FIG. 2 is a schematic block diagram of the components of a system for anonymously linking a plurality of data records according to one embodiment of the invention.

Referring now to FIG. 2, the memory devices 18 of FIG. 1 are depicted as storing therein a system 50 for anonymously linking a plurality of data records 52. The data records 52 may be stored within an input database 54 or other suitable location. The input database 54 may comprise, for example, a conventional relational database management system (RDBMS), such as one available from ORACLE®, SYBASE®, or the like. In alternative embodiments, the input database 54 may comprise a flat file, a table, or other conventional data structure.

In one embodiment, each data record 52 includes a plurality of identifying elements 56 for identifying an individual to whom the record 52 pertains. The identifying elements 56 may include, for example, a name, a birth date, an address, a ZIP code, a telephone number, a healthcare identifier, and the like. A variety of different or additional identifying elements 56 may be provided within the scope of the invention.

In certain presently preferred embodiments, the system 50 includes a plurality of modules containing executable code for performing the methods described herein. Although the modules are illustrated as separate functional units, the various modules may be combined or integrated into a single software application or device. Likewise, the functionality of any one module may be implemented using two or more modules.

In one embodiment, the system 50 includes a plurality of identity reference encoding modules 58. For example, as illustrated in the FIG. 2, the system 50 may include first and second identity reference encoding modules 58A–B. However, three or more encoding modules 58 may be provided in alternative embodiments.

Preferably, the first identity reference encoding module 58A encodes a first encoded identity reference 60A (designated "EIR" in FIG. 2) from a first subset 62A of the identifying elements 56 of a data record 52. The first encoded identity reference 60A may comprise a one-way hash of the first subset 62A, which may be generated, for example, by applying a cryptographic hash function, such as SHA1 (Secure Hash Algorithm 1) or the like.

Defined by the National Institute of Standards and Technology (NIST), SHA1 is a cryptographic standard having a cryptographic strength of 160 bits, which makes SHA1 computationally infeasible to reverse. Accordingly, recovering the first subset 62A from the first encoded identifying reference 60A is practically impossible. However, other well known hashing schemes, such as MD5 (Message Digest 5), may be used within the scope of the invention.

In alternative embodiments, different encoding techniques may be used, such as encrypting the first subset 60A using symmetric or public key cryptographic algorithms. Nevertheless, the selected encoding technique preferably generates a one-to-one correspondence between the subsets 62 and the encoded identity references 60. In other words, no two subsets 62 share the same encoded identity reference 60, or at least the probability of an unintended collision is acceptably low.

Likewise, the second identity reference encoding module 58B preferably encodes a second encoded identity reference 60B from a second subset 62B of the identifying elements 56 of the same data record 52. Either the same or a different encoding technique may be used to encode the second encoded identity reference 60B.

In one embodiment, the first and second subsets 62A–B may be disjoint, i.e. have no identifying elements 56 in common, or, as depicted, may share one or more common identifying elements 56. Preferably, however, the two subsets 62A–B are not identical, since the resulting encoded identity references 60 would likewise be identical.

For example, the first subset 62A may comprise a name, a birth date, and a ZIP code, while the second subset 62B may comprise a healthcare identifier and a birth date. In an alternative embodiment, a subset 62A–B may include a telephone number and a birth date. A variety of different combinations of identifying elements 56 may be provided within the scope of the invention.

Preferably, however, the subsets 62A–B are selected such that each data record 52 includes all of the identifying elements 56 of each subset 62A–B. Moreover, the same subsets 62A–B are preferably used in calculating the first and second encoded identity references 60A–B for each record 52 processed by the system 50.

In alternative embodiments, the system 50 may include one or more additional identity reference encoding modules 58 as needed. Each additional encoding module 58 may be used to encode a different subset 62 of identifying elements 56 to produce an additional encoded identity reference 60. The use of additional encoded identity references 60 may increase, in certain embodiments, the accuracy of identifying all of the data records 52 pertaining to the same individual.

In one embodiment, the system 50 also includes an anonymization code lookup module 64. Preferably, the anonymization code lookup module 64 determines whether each of the first and second encoded identity references 60A–B has an assigned anonymization code 66 (designated "AC" in FIG. 2). In one embodiment, each individual associated with a data record 52 is uniquely represented within the system 50 by an anonymization code 66. In alternative embodiments, an anonymization code 66 may be used to represent more than one individual. For example, a unique anonymization code 66 may be assigned to a particular group or population.

In one embodiment, an anonymization code database 68 stores the anonymization code 66 assignments for the encoded identity references 60. The anonymization code database 68 may be implemented within a standard RDBMS, such as ORACLE®. However, as used herein, the term "database" may include any suitable data structure or system for storing the anonymization code 66 assignments. For example, a table or other similar data structure within the memory devices 18 may be used for such a purpose. The anonymization code 66 may comprise a serial number, in one embodiment, which may facilitate rapid querying of the database 68.

In one embodiment, the anonymization code database 68 may be conceptualized as an "anonymous index," which may link each encoded identity reference 60 to an assigned anonymization code 66. Because the encoded identity references 60 may not be reversed to reveal an individual's identity, the anonymization code database 68 is conceptually very different from conventional approaches, such as a Master Patient Index (MPI), which links personally identifiable information to assigned patient codes.

The anonymization code lookup module 64 is depicted as including a database query module 70. In one embodiment, the database query module 70 queries the anonymization code database 68 to retrieve the anonymization code 66, if any, for each of the first and second encoded identity references 60A–B. Where, for example, the database 68 comprises a flat file or a table, the database query module 70 may simply perform a lookup operation within the flat file or the table.

In the depicted embodiment, the system 50 also includes an anonymization code assignment module 72. In response to neither of the encoded identity references 60A–B having an assigned anonymization code 66 in the anonymization code database 68, the anonymization code assignment module 72 preferably assigns a new, identical anonymization code 66 to the first and second encoded identity references 60A–B. In an embodiment in which three or more encoded identity references 60 are generated, the new anonymization code 66 is preferably assigned to each of the encoded identity references 60.

If, however, one encoded identity reference 60 has an assigned anonymization code 66, while the other encoded identity reference 60 does not, the anonymization code assignment module 74 preferably assigns the same anonymization code 66 found to be associated with the one encoded identity references 60 to the other encoded identity reference 60. In an embodiment in which three or more encoded identity references 60 are generated, the anonymization code 66 of one encoded identity reference 60 may be assigned to each of the other encoded identity references that lack an anonymization code 66.

The anonymization code assignment module 72 is depicted as including an anonymization code generation module 74 and a database update module 76. The anonymization code generation module 74 is used, in one embodiment, to generate the new, unique anonymization code 66 to represent an individual, as previously described. Preferably, the database update module 76 is used to update the anonymization code database 68 with the assigned anonymization code 66 corresponding to the first and second encoded identity references 60A–B, as described above.

The system 50 may also include an identifying element removal module 78 and an anonymization code insertion module 80. In one embodiment, the identifying element removal module 78 removes the identifying elements 56 of the data record 52, resulting in an anonymized data record 82.

In certain embodiments, however, the inclusion of an identifying element removal module 78 is optional. For example, it may be desirable simply to identify and link a plurality of data records 52 pertaining to the same individual without anonymizing the data record 52. Likewise, in alternative embodiments, the identifying element removal process may be more efficiently performed by a third party or at a later time.

In one embodiment, the anonymization code insertion module 80 inserts the assigned anonymization code 66 into anonymized data record 82. Since, according to one embodiment, each anonymized record 82 pertaining to the same individual includes the same assigned anonymization code 66, the anonymized records 84 are effectively linked. Of course, other linking mechanisms, such as pointers and the like, may be used within the scope of the invention. In one embodiment, the anonymized data record 82 may be stored within an output database 84 or similar location.

Figure 3:
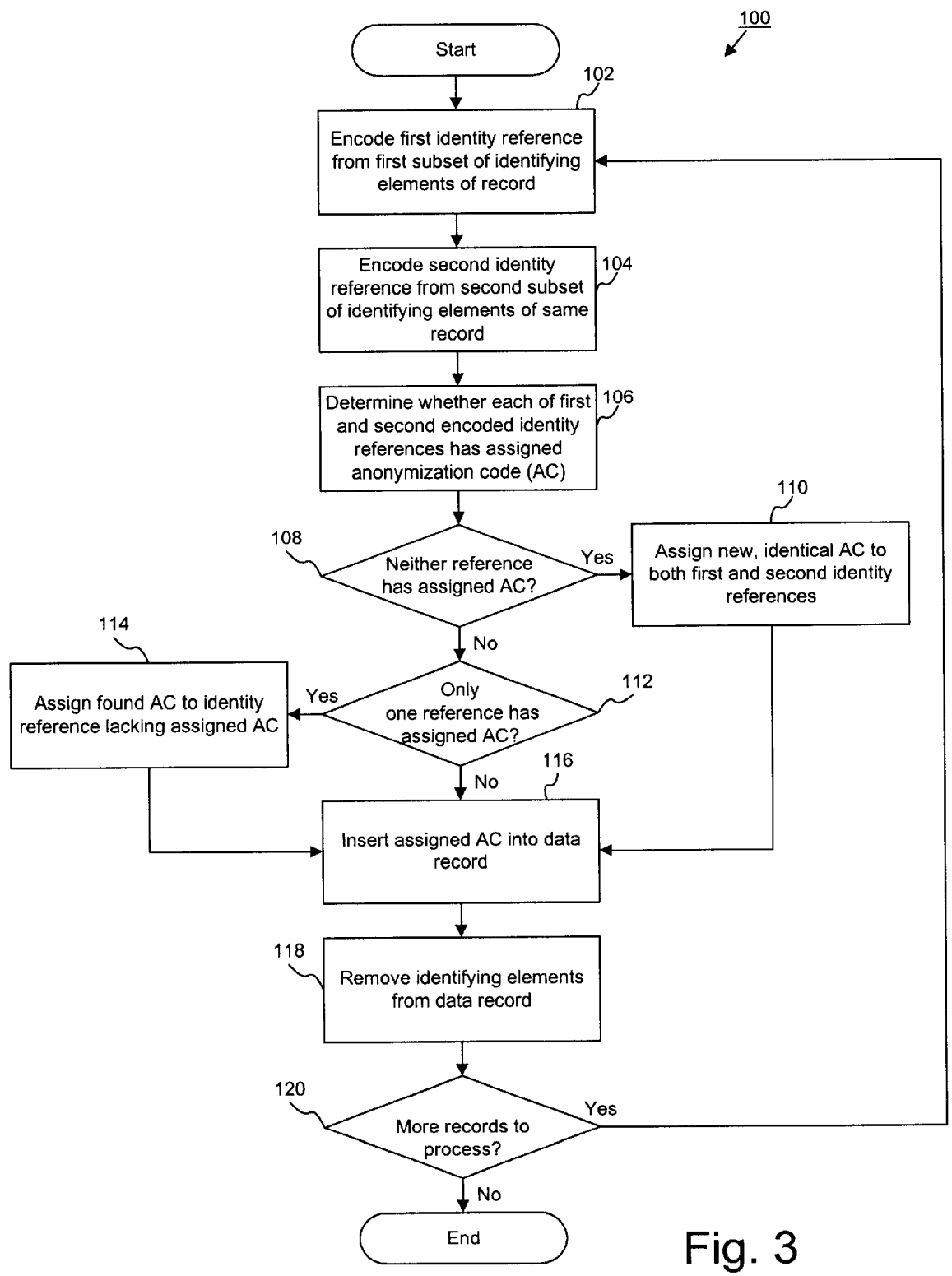
FIG. 3 is a schematic flow chart of a method for anonymously linking a plurality of data records according to one embodiment of the invention.

Referring now to FIG. 3, a schematic flowchart illustrates one embodiment of a method 100 for anonymously linking a plurality of data records 52. The method 100 preferably begins by encoding 102 a first encoded identity reference 60A from a first subset 62A of the identifying elements 56 of a record 52. The record 52 may be obtained, for example, from an input database 54 or the like. As noted above, the first encoded identity reference 60A may comprise a one-way hash of the first subset 62A, which may be generated, for example, by applying a cryptographic hash function, such as SHA1 or the like.

Thereafter, the method 100 preferably continues by encoding 104 a second encoded identity reference 60B from a second subset 62B of the identifying elements 56 of the same data record 52. As previously noted, either the same or a different encoding technique may be used to encode the second encoded identity reference 60B.

In one embodiment, the first and second subsets 62A–B may be disjoint, or may have one or more identifying elements 56 in common. Preferably, however, the subsets 62A–B are not identical. Moreover, the selection of identifying elements 56 within the subsets 62A–B should remain constant for every record 52 processed using the method 100.

While only two encoded identity references 60A–B are generated in one embodiment, three or more encoded identity references 60 may be generated within the scope of the invention. As previously noted, the use of additional encoded identity references 60 may increase, in certain embodiments, the accuracy of identifying all of the data records 52 pertaining to the same individual.

In one embodiment, the method 100 continues by determining 106 whether each of the first and second encoded identity references 60A–B has an assigned anonymization code 66. As noted above, the anonymization code 66 is preferably used to uniquely identity an individual associated with a record 52.

A check 108 is then made as to whether neither of the encoded identity references 60A–B has an assigned anonymization code 66. If neither reference 60A–B has an assigned anonymization code 66, the method 100 continues by assigning 110 new, identical anonymization codes 66 to both the first and second encoded identity references 60A–B.

If, however, one or both of the encoded identity references 60A–B has an assigned anonymization code 66, the method 100 continues by determining 112 whether one of the encoded identity references 60 has an assigned anonymization code 66 while the other encoded identity reference 60 does not. If so, the method 100 continues by assigning 114 the same anonymization code 66 found to be associated with one of the encoded identity references 60 to the encoded identity reference 60 lacking an assigned anonymization code 66.

For example, if the first encoded identity reference 60A has an assigned anonymization code 66, but the second encoded identity reference 60B does not, the second encoded identity reference 60B is assigned the same anonymization code 66 as the first encoded identity reference 60A. In embodiments including three or more encoded identity references 60, the anonymization code 66 of one encoded identity reference 60 may be assigned to all of the encoded identity references 60 that lack an assigned anonymization code 66.

After any of steps 110, 114, or 116, the method 100 continues by inserting 116 the assigned anonymization code 66 into the data record 52. In one embodiment, the method 100 may additionally remove 118 the identifying elements 56 of the data record 52 to create an anonymized data record 82.

Preferably, a check 120 is then made as to whether more records 52 remain to be processed, e.g., whether more records 52 remain in the input database 54. If so, the method 100 returns to step 102; otherwise, the method 100 is complete.

The method 100 of FIG. 3 is more fully illustrated by the following example in the context of anonymously linking a plurality of existing healthcare transaction records 52. However, as previously noted, the records 52 need not involve healthcare. Moreover, rather than processing existing records 52, the illustrated method 100 may be performed each time a patient visits a healthcare facility and a new healthcare transaction record 52 is created.

For purposes of the following example, the first subset 62A of identifying elements 56 includes a name, a date of birth (DOB), and a ZIP code. The second subset 62B preferably includes a healthcare identifier (such as a medical plan number) and a DOB. While the subsets 62A–B are depicted as including a common identifying element 56, i.e. DOB, the invention is not limited in this respect.

Initially, the system 50 may obtain a first record 52. As previously explained, the record 52 may be obtained from an input database 52, or, as noted immediately above, at the time the record 52 is generated. For illustration purposes, the first subset 62A may include "John Doe," "Dec. 25, 1950," and "73112," which correspond to the name, DOB, and ZIP identity elements 56, respectively. Likewise, the second subset 62B may include "446-12-3456-01" and "Dec. 25, 1950," which correspond to the healthcare identifier and DOB identity elements 56.

After the record 52 is obtained, the first and second encoded identity references 60A–B are preferably encoded from the first and second subsets 62A–B, respectively. As noted above, the encoded identity references 60A–B are preferably one-way hashes of the corresponding subsets 62A–B. For example, the first subset 62A may be encoded as "a2d6637f . . . 4ab16393," while the second subset 62B may be encoded as "5d18ec82 . . . 95168ad6."

The anonymization code database 68 is then consulted to determine whether the record 52 pertains to a known patient:

| Database 68 | | |
| --- | --- | --- |
| Name, DOB, ZIP (Subset 62A) | First encoded identity reference 60A | Anonymization code 66 |
| John Doe, 12/25/1950, 73112 | → a2d6637f...4ab16393 | → ? |
| Healthcare identifier, DOB (Subset 62B) | Second encoded identity reference 60B | |
| 446-12-345-01, 12/25/1950 | → 5d18ec82...95168ad6 | → ? |

Since, as illustrated above, neither of the encoded identity references 60 is found in the database 68, a new anonymization code 66 is preferably created (e.g. 000567123) and stored in the database 68 in association with the first and second encoded identity references 60A–B. As a result, the database 68 includes the following entries for the new patient:

| Database 68 | | |
| --- | --- | --- |
| Name, DOB, ZIP (Subset 62A) | First encoded identity reference 60A | Anonymization code 66 |
| John Doe, 12/25/1950, 73112 | → a2d6637f...4ab16393 | → 000567123 |
| Healthcare identifier, DOB (Subset 62B) | Second encoded identity reference 60B | |
| 446-12-3456-01, 12/25/1950 | → 5d18ec82...95168ad6 | → 000567123 |

Unlike an MPI, the various identifying elements 56 need not be retained within the database 68, but are illustrated herein simply for clarity of explanation. Only the first and second encoded identity reference 60A–B and the corresponding anonymization code 66 are actually stored in the database 68.

After the anonymization codes 66 are stored, the identifying elements 56 of the record 52 may be removed using conventional techniques to generate an anonymized data record 82. In addition, the anonymization code 66 may be inserted into the anonymized record 82 in order to provide a link to the other anonymized records 82 pertaining to the same patient.

Next, the system 50 may obtain a second record 52. For purposes of example, the record 52 relates to the same patient, but is derived from a different data source (e.g. pharmacy vs. hospital), which uses a different healthcare identifier (e.g. pharmacy PBM card identifier vs. medical identifier). As a result, the second encoded identity reference 60B is different from that of the first record 52 because of the different healthcare identifier:

| Database 68 | | |
|---|---|---|
| Name, DOB, ZIP (Subset 62A) | First encoded identity reference 60A | Anonymization code 66 |
| John Doe, 12/25/1950, 73112 → | a2d6637f...4ab16393 → | 000567123 |
| Healthcare identifier, DOB (Subset 62B) | Second encoded identity reference 60B | |
| 4008912349852, 12/25/1950 → | 15bfb00f...d0170171 → | ? |

A check is made of the anonymization code database 68, which reveals that the second encoded identity reference 60B does not have an assigned anonymization code 66. Accordingly, the system 50 preferably assigns the same anonymization code 66 (e.g. 000567123) to the second encoded identity reference 60B, storing the anonymization code 66 in the database 68. As illustrated below, the database 68 now includes the following entries related to the same patient:

| Database 68 | | |
|---|---|---|
| Name, DOB, ZIP (Subset 62A) | First encoded identity reference 60A | Anonymization code 66 |
| John Doe, 12/25/1950, 73112 → | a2d6637f...4ab16393 → | 000567123 |
| Healthcare identifier, DOB (Subset 62B) | Second encoded identity reference 60B | |
| 446-12-3456-01, 12/25/1950 → | 5d18ec82...95168ad6 → | 000567123 |
| 4008912349852, 12/25/1950 → | 15bfb00f...d0170171 → | 000567123 |

Next, the system 50 may obtain a third record 52. For illustration purposes, the record 52 pertains to the same patient, but the patient has moved to a different ZIP code:

| Database 68 | | |
|---|---|---|
| Name, DOB, ZIP (Subset 62A) | First encoded identity reference 60A | Anonymization code 66 |
| John Doe, 12/25/1950, 73101 → | 64f7f382...cda00359 → | ? |
| Identifier, DOB (Subset 62B) | Second encoded identity reference 60B | |
| 4008912349852, 12/25/1950 → | 15bfb00f...d0170171 → | 000567123 |

As before, the anonymization code database 68 is consulted. Since the first encoded identity reference 60A does not have an anonymization code 66, the system 50 preferably assigns the same anonymization code 66 (e.g. 000567123) to the first encoded identity reference 60A, storing the anonymization code 66 in the database 68. The same situation may occur, for example, when a patient changes his or her name (e.g. marriage, divorce, etc.). As illustrated below, the database 68 now includes the following entries pertaining to the same patient:

| Database 68 | | |
|---|---|---|
| Name, DOB, ZIP (Subset 62A) | First encoded identity reference 60A | Anonymization code 66 |
| John Doe, 12/25/1950, 73112 | → a2d6637f...4ab16393 | → 000567123 |
| John Doe, 12/25/1950, 73101 | → 64f7f382...cda00359 | → 000567123 |
| Healthcare identifier, DOB (Subset 62B) | Second encoded identity reference 60B | |
| 446-12-3456-01, 12/25/1950 | → 5d18ec82...95168ad6 | → 000567123 |
| 4008912349852, 12/25/1950 | → 15bfb00f...d0170171 | → 000567123 |

Next, the system 50 may obtain a fourth record 52. In this case, the record 52 relates to a different patient. However, for illustration purposes, the record 52 relates to the wife of the first patient, who uses the same healthcare identifier (which is often the case in medical plans):

| Database 68 | | |
|---|---|---|
| Name, DOB, ZIP (Subset 62A) | First encoded identity reference 60A | Anonymization code 66 |
| Jane Doe, 07/04/1951, 73112 | → 6e318f2d...8c04472f | → ? |
| Healthcare identifier, DOB (Subset 62B) | Second encoded identity reference 60B | |
| 4008912349852, 07/04/1951 | → 68e36eb9...6bd29ed1 | → ? |

As before, the anonymization code database 68 is consulted to determine whether the record 52 pertains to a known patient. However, as illustrated above, neither of the encoded identity references 60 is found in the database 68. Because the second encoded identity reference 60B is derived from the healthcare identifier in conjunction with the date of birth, even if two members of the same family share the same healthcare identifier, the date of birth will cause the encoded identity reference 60, in each instance, to be different.

As a result, the system 50 preferably assigns a new anonymization code 66 (e.g. 000432765) to the first and second encoded identity references 60A–B, resulting in a new patient in the system 50.

| Database 68 | | |
|---|---|---|
| Name, DOB, ZIP (Subset 62A) | First encoded identity reference 60A | Anonymization code 66 |
| Jane Doe, 07/04/1951, 73112 | → 6e318f2d...8c04472f | → 000432765 |
| Healthcare identifier, DOB (Subset 62B) | Second encoded identity reference 60B | |
| 4008912349852, 07/04/1951 | → 68e36eb9...6bd29ed1 | → 000432765 |

As illustrated below, the database 68 now includes the following entries pertaining to the two patients:

| Database 68 | | |
|---|---|---|
| Name, DOB, ZIP (Subset 62A) | First encoded identity reference 60A | Anonymization code 66 |
| John Doe, 12/25/1950, 73112 | → a2d6637f...4ab16393 | → 000567123 |
| John Doe, 12/25/1950, 73101 | → 64f7f382...cda00359 | → 000567123 |
| Jane Doe, 07/04/1951, 73112 | → 6e318f2d...8c04472f | → 000432765 |
| Healthcare identifier, DOB (Subset 62B) | Second encoded identity reference 60B | |
| 446-12-3456-01, 12/25/1950 | → 5d18ec82...95168ad6 | → 000567123 |
| 4008912349852, 12/25/1950 | → 15bfb00f...d0170171 | → 000567123 |
| 4008912349852, 07/04/1951 | → 68e36eb9...6bd29ed1 | → 000432765 |

In the improbable case of finding a collision of two individuals sharing the same first subset 62A of identifying elements 56, the database lookup will indicate that the first encoded identity reference 60A and second encoded identity reference 60B are inconsistent with each other and result in two different anonymization codes 66. In this case, the second encoded identity reference 60B may be given preference in order to assign the anonymization code 66 of the individual.

Based on the foregoing, the present invention offers numerous advantages not found in conventional approaches. For example, using two or more encoded identity references 60, and leveraging a known encoded identity reference 60 to derive the anonymization code 66 to be assigned to a new encoded identity reference 60, assures that the multiple identities of a patient are kept in synchronization. As long as a patient does not change the healthcare identifier and the name at the same time, which would normally signify a new patient, the anonymous identity of the patient may be automatically preserved via the assigned anonymization code 66.

The multiple encoded identity references 60 build the anonymization code database 68 automatically, based on the data itself, and allow tracking of the anonymous identity of the individuals even when they have multiple changing identity elements 56. The only requirement is that from one time to the next, at least one of the encoded identity references 60 remain constant.

Another advantage is that the anonymization code database 68, itself, is anonymous and cannot be used to reverse the process, since the entries in the database 68 are, for example, cryptographic hashes and anonymization codes 66. Thus, the database 68 is not subject to compromise, even by a malicious insider. Accordingly, the foregoing process is superior to the traditional processes of matching names in a database that contains identifiable patient information, such as a Master Patient Index.

While the system 50 and method 100 of certain presently preferred embodiments of the invention are described in the context of healthcare, various other industries may benefit from the principles disclosed herein. For example, credit card transactions of an individual may be anonymously linked in order to perform research studies on spending habits without compromising an individual's privacy. Similar benefits may be realized in the banking industry, in the travel industry, and a variety of other industries that have access to electronically-stored information pertaining to a large number of individuals.

The present invention may be embodied in other specific forms without departing from its scope or essential characteristics. The described embodiments are to be considered in all respects only as illustrative and not restrictive. The scope of the invention is, therefore, indicated by the appended claims rather than by the foregoing description.

What is claimed and desired to be secured by United States Letters Patent is:

1. A computer-implemented method for anonymously linking a plurality of data records, each data record comprising a plurality of elements for identifying an associated individual, the method comprising:
   for each of the plurality of data records:
      encoding a first encoded identity reference from a first subset of the identifying elements of a data record;
      encoding a second encoded identity reference from a second subset of the identifying elements of the data record;
      assigning to each of the first and second encoded identity references an identical anonymization code for anonymously representing the individual associated with the data record; and
      inserting the assigned anonymization code into the data record.

2. The method of claim 1, further comprising:
   removing the plurality of identifying elements from the data record.

3. The method of claim 1, wherein assigning to each of the first and second encoded identity references an identical anonymization code comprises:
   determining whether each of the first and second encoded identity references has an assigned anonymization code; and
   in response to neither the first nor second encoded identity references having an assigned anonymization code:
      providing a new anonymization code; and
      assigning the new anonymization code to both the first and second encoded identity references.

4. The method of claim 3, wherein a database stores at least one anonymization code assigned to an encoded identity reference, and wherein determining whether each of the first and second encoded identity references has an assigned anonymization code comprises:
   querying the database for an anonymization code assigned to each of the first and second encoded identity references.

5. The method of claim 3, wherein a database stores anonymization codes assigned to encoded identity references, and wherein assigning the new anonymization code to both the first and second encoded identity references comprises:
   storing the new anonymization code in the database; and
   associating, within the database, the new anonymization code with the first and second encoded identity references.

6. The method of claim 1, wherein assigning to each of the first and second encoded identity references an identical anonymization code comprises:
   determining whether each of the first and second encoded identity references has an assigned anonymization code; and
   in response to the first encoded identity reference having an anonymization code and the second encoded identity reference not having an assigned anonymization code:
      assigning the second encoded identity reference the same anonymization code assigned to the first encoded identity reference.

7. The method of claim 6, wherein a database stores anonymization codes assigned to encoded identity references, and wherein assigning the second encoded identity reference the same anonymization code assigned to the first encoded identity reference comprises:
   associating, within the database, the second encoded identity reference with assigned anonymization code of the first encoded identity reference.

8. The method of claim 1, further comprising:
   repeating the calculating and assigning steps for each of the plurality of data records.

9. The method of claim 1, wherein encoding a first encoded identity reference comprises:
   encoding the first subset of identifying elements using a one-way hash function.

10. The method of claim 1, wherein encoding a second encoded identity reference comprises:

encoding the second subset of identifying elements using a one-way hash function.

11. The method of claim 1, wherein one of the first and second subsets of identifying elements comprises a name, a birth date, and a zip code.

12. The method of claim 1, wherein one of the first and second subsets of identifying elements comprises a healthcare identifier and a birth date.

13. The method of claim 1, wherein one of the first and second subsets of identifying elements comprises a telephone number and birth date.

14. The method of claim 1, wherein the plurality of data records are selected from the group consisting of healthcare transaction records and financial transaction records.

15. A system for anonymously linking a plurality of data records, each data record comprising a plurality of elements for identifying an associated individual, the system comprising:

a first identity reference encoding module configured to calculate a first encoded identity reference from a first subset of the identifying elements of a data record;

a second identity reference encoding module configured to calculate a second encoded identity reference from a second subset of the identifying elements of the data record;

an anonymization code assignment module configured to assign to each of the first and second encoded identity references an identical anonymization code for anonymously representing the individual associated with the record; and an anonymization code insertion module configured to insert the assigned anonymization code into the data record;

wherein the system is configured to calculate first and second encoded identity references, and assign and insert anonymization codes for each of the plurality of data records.

16. The system of claim 15, further comprising:

an identifying element removal module configured to remove the plurality of identifying elements from the data record.

17. The system of claim 15, wherein the anonymization code assignment module comprises:

an anonymization code lookup module configured to determine whether each of the first and second encoded identity references has an assigned anonymization code; and an anonymization code generation module configured, in response to neither the first nor second encoded identity references having an assigned anonymization code, to provide a new anonymization code and assign the new anonymization code to both the first and second encoded identity references.

18. The system of claim 17, further comprising:

an anonymization code database configured to store at least one anonymization code assigned to an encoded identity reference.

19. The system of claim 18, wherein the anonymization code lookup module comprises:

a database querying module configured to query the anonymization code database for an anonymization code for each of the first and second encoded identity references.

20. The system of claim 18, wherein the anonymization code assignment module comprises:

a database update module configured to store the new anonymization code in the database and associate, within the database, the new anonymization code with the first and second encoded identity references.

21. The system of claim 15, wherein the anonymization code assignment module comprises:

an anonymization code lookup module configured to determine whether each of the first and second encoded identity references has an assigned anonymization code; and an anonymization code generation module configured, in response to the first encoded identity reference having an anonymization code and the second encoded identity reference not having an assigned anonymization code, to assign the second encoded identity reference the same anonymization code assigned to the first encoded identity reference.

22. The system of claim 21, wherein an anonymization code database stores at least one anonymization code assigned to an encoded identity reference, and wherein the anonymization code assignment module comprises:

a database update module configured to associate, within the database, the second encoded identity reference with the same anonymization code assigned to first encoded identity reference.

23. The system of claim 15, wherein the first encoded identity reference comprises a one-way hash of the first subset of identifying elements.

24. The system of claim 15, wherein the second encoded identity reference comprises a one-way hash of the second subset of identifying elements.

25. The system of claim 15, wherein one of the first and second subsets of identifying elements comprises a name, a birth date, and a zip code.

26. The system of claim 15, wherein one of the first and second subsets of identifying elements comprises a healthcare identifier and a birth date.

27. The system of claim 15, wherein one of the first and second subsets of identifying elements comprises a telephone number and a birth date.

28. The system of claim 15, wherein the plurality of data records are selected from the group consisting of healthcare transaction records and financial transaction records.

29. An article of manufacture comprising a program storage medium readable by a processor and embodying one or more instructions executable by the processor to perform a computer-implemented method for anonymously linking a plurality of data records, each data record comprising a plurality of elements for identifying an associated individual, the method comprising:

for each of the plurality of data records:
encoding a first encoded identity reference from a first subset of the identifying elements of a data record;
encoding a second encoded identity reference from a second subset of the identifying elements of the data record;
assigning to each of the first and second encoded identity references an identical anonymization code for anonymously representing the individual associated with the data record; and
inserting the assigned anonymization code into the data record.

30. The article of manufacture of claim 29, the method further comprising:

removing the plurality of identifying elements from the data record.

31. The article of manufacture of claim 29, wherein assigning to each of the first and second encoded identity references an identical anonymization code comprises:
  determining whether each of the first and second encoded identity references has an assigned anonymization code; and
  in response to neither the first nor second encoded identity references having an assigned anonymization code:
    providing a new anonymization code; and
    assigning the new anonymization code to both the first and second encoded identity references.

32. The article of manufacture of claim 31, wherein a database stores at least one anonymization code assigned to an encoded identity reference, and wherein determining whether each of the first and second encoded identity references has an assigned anonymization code comprises:
  querying the database for an anonymization code assigned to each of the first and second encoded identity references.

33. The article of manufacture of claim 31, wherein a database stores at least one anonymization code assigned to an encoded identity reference, and wherein assigning the new anonymization code to both the first and second encoded identity references comprises:
  storing the new anonymization code in the database; and
  associating, within the database, the new anonymization code with the first and second encoded identity references.

34. The article of manufacture of claim 29, wherein assigning to each of the first and second encoded identity references an identical anonymization code comprises:
  determining whether each of the first and second encoded identity references has an assigned anonymization code; and
  in response to the first encoded identity reference having an anonymization code and the second encoded identity reference not having an assigned anonymization code:
    assigning the second encoded identity reference the same anonymization code assigned to the first encoded identity reference.

35. The article of manufacture of claim 34, wherein a database stores at least one anonymization code assigned to an encoded identity references, and wherein assigning the second encoded identity reference the same anonymization code assigned to the first encoded identity reference comprises:
  associating, within the database, the second encoded identity reference with assigned anonymization code of the first encoded identity reference.

36. The article of manufacture of claim 29, the method further comprising:
  repeating the calculating and assigning steps for each of the plurality of data records.

37. The article of manufacture of claim 29, wherein encoding a first encoded identity reference comprises:
  encoding the first subset of identifying elements using a one-way hash function.

38. The article of manufacture of claim 29, wherein encoding a second encoded identity reference comprises:
  encoding the second subset of identifying elements using a one-way hash function.

39. The article of manufacture of claim 29, wherein one of the first and second subsets of identifying elements comprises a name, a birth date, and a zip code.

40. The article of manufacture of claim 29, wherein one of the first and second subsets of identifying elements comprises a healthcare identifier and a birth date.

41. The article of manufacture of claim 29, wherein one of the first and second subsets of identifying elements comprises a telephone number and birth date.

42. The article of manufacture of claim 29, wherein the plurality of data records are selected from the group consisting of healthcare transaction records and financial transaction records.

* * * * *